United States Patent

Honjo

[19]

[11] Patent Number: 6,111,648
[45] Date of Patent: Aug. 29, 2000

[54] BLACK ROLL FOR OPTICAL MEASUREMENT, THIN FILM FORMING APPARATUS INCLUDING THE DAME, AND THIN FILM FORMING METHOD USING THE SAME

[75] Inventor: Yoshiharu Honjo, Kanagawa, Japan

[73] Assignee: Sony Corporation, Tokyo, Japan

[21] Appl. No.: 09/369,283

[22] Filed: Aug. 6, 1999

[30] Foreign Application Priority Data

Aug. 19, 1998 [JP] Japan ................ P10-233038

[51] Int. Cl.[7] .................................. G01B 11/06
[52] U.S. Cl. ............................ 356/381; 427/428
[58] Field of Search .................. 356/381, 372, 356/389; 427/428

[56] References Cited

U.S. PATENT DOCUMENTS

| | | | |
|---|---|---|---|
| 4,969,738 | 11/1990 | Mann | 356/244 |
| 5,212,596 | 5/1993 | Andrus | 359/614 |
| 5,970,613 | 10/1999 | Mori et al. | 29/888.43 |
| 5,989,671 | 11/1999 | Nakayama et al. | 428/64.3 |

Primary Examiner—Robert H. Kim
Assistant Examiner—Layla Lauchman
Attorney, Agent, or Firm—Hill & Simpson

[57] ABSTRACT

Disclosed is a black roll for optical measurement, which is used for a process of moving a film substrate around the black roll, and measuring optical characteristics of a thin film formed on the film substrate by using an optical monitor disposed in proximity to the film substrate. The black roll includes: a rotating cylinder colored in black, with the circumferential surface of which the film substrate is in close-contact; wherein the rotating cylinder has at least one groove formed in the circumferential surface of the rotating cylinder in such a manner as to extend in the circumferential direction, the groove being adapted to absorb light which is emitted from the optical monitor, passing through the film substrate, and is made incident on the black roll. The black roll is effective to eliminate almost all reflectance of light from the black roll in the case of measuring the reflectance of an optical thin film formed on a film substrate moved in such a manner as to be in close-contact with the black roll.

9 Claims, 3 Drawing Sheets

કારણ

# BLACK ROLL FOR OPTICAL MEASUREMENT, THIN FILM FORMING APPARATUS INCLUDING THE DAME, AND THIN FILM FORMING METHOD USING THE SAME

RELATED APPLICATION DATA

The present application claims priority to Japanese Application No. P10-233038 filed Aug. 19, 1998 which application is incorporated herein by reference to the extent permitted by law.

BACKGROUND OF THE INVENTION

The present invention relates to a black roll for optical measurement, a thin film forming apparatus including the black roll, and a thin film forming method using the black roll. In particular, the present invention relates to a black roll for optical measurement improved to eliminate almost all reflection of light from the surface of the black roll, a thin film forming apparatus including the black roll, and a thin film forming method using the black roll.

In recent years, a method of producing various functional film bodies by forming a desired optical thin film on a plastic film substrate becomes widely available. The method requires a technique of measuring optical characteristics of the optical thin film formed on the plastic film substrate in-situ while moving the plastic film substrate. To measure optical characteristics of an optical thin film formed on a plastic film substrate in-situ during operation of forming the optical thin film on the plastic film substrate, a so-called black roll for optical measurement is generally used. The black roll is composed of a rotating cylinder colored in black for eliminating adverse effect of reflection of measuring light from the surface of the rotating cylinder. A plastic film substrate on which an optical thin film has been formed is moved in such a manner as to be in close-contact with the rotating black roll for suppressing a vertical change in the surface of the plastic film substrate, and optical characteristics such as a reflectance of the optical thin film are measured using an optical monitor.

For an optical thin film having a low reflectance, however, the method of using the above related art black roll causes a problem. Since the reflectance of light from the surface of the optical thin film is as low as almost close to zero in a visible light region, the reflectance of the black roll, which is in a range of 0.01 to 0.05% and is varied if the surface of the black roll is uneven, gives a measurement error to the result of measuring the reflectance of the optical thin film. In other words, according to the method using the related art black roll, although it is intended to measure only the reflection of light from the optical thin film formed on the surface of the plastic film substrate in close-contact with the black roll, the measured value contains a small degree of reflection of light from the black roll.

If the reflectance of the black roll is constant, the reflectance of an optical thin film can be accurately obtained by subtracting a previously measured reflectance of the black roll from the result of measuring the reflectance of the optical thin film; however, since the surface roughness of the black roll is large, the reflectance of the black roll is unstable. Also, in the case of measuring the reflectance of the optical thin film in-situ by using an optical monitor, the reflectance data obtained in real time is poor in reliability because of non-uniformity of color on the surface of the black roll. In this way, a deviation may easily occur between a value measured in-situ by using the black roll and a value measured without use of the black roll, and therefore, according to the method using the related art black roll, it becomes difficult to stably measure the reflectance of the optical thin film formed on the plastic film substrate in-situ during operation of forming the optical thin film on the plastic film substrate.

SUMMARY OF THE INVENTION

An object of the present invention is to provide a black roll for optical measurement, which is capable of eliminating almost all reflectance of light from the black roll in the case of measuring in-situ the reflectance of an optical thin film formed on a film substrate moved in such a manner as to be in close-contact with the black roll, a thin film forming apparatus including the black roll, and a thin film forming method using the black roll.

According to a first aspect of the present invention, there is provided a black roll for optical measurement, which is used for a process of moving a film substrate around the black roll, and measuring optical characteristics of a thin film formed on the film substrate by using an optical monitor disposed in proximity to the film substrate, the black roll including: a rotating cylinder colored in black, with the circumferential surface of which the film substrate is in close-contact; wherein the rotating cylinder has at least one groove formed in the circumferential surface of the rotating cylinder in such a manner as to extend in the circumferential direction, the groove being adapted to absorb light which is emitted from the optical monitor, passing through the film substrate, and is made incident on the black roll.

According to a second aspect of the present invention, there is provided a thin film forming apparatus including a black roll for optical measurement, which is used for a process of moving a film substrate around the black roll, and measuring optical characteristics of a thin film formed on the film substrate by using an optical monitor disposed in proximity to the film substrate, the black roll including: a rotating cylinder colored in black, with the circumferential surface of which the film substrate is in close-contact; wherein the rotating cylinder has at least one groove formed in the circumferential surface of the rotating cylinder in such a manner as to extend in the circumferential direction, the groove being adapted to absorb light which is emitted from the optical monitor, passing through the film substrate, and is made incident on the black roll.

According to a third aspect of the present invention, there is provided a thin film forming method using a black roll for optical measurement, comprising the steps of: moving a film substrate around the black roll; and measuring optical characteristics of a thin film formed on the film substrate by using an optical monitor disposed in proximity to the film substrate; wherein the black roll includes a rotating cylinder colored in black, with the circumferential surface of which the film substrate is in close-contact; and the rotating cylinder has at least one groove formed in the circumferential surface of the rotating cylinder in such a manner as to extend in the circumferential direction, the groove being adapted to absorb light which is emitted from the optical monitor, passing through the film substrate, and is made incident on the black roll.

In the above black roll, thin film forming apparatus, and thin film forming method, preferably, the cross-section of the groove, taken along a plane including the center axis of the rotating cylinder, has a shape extending in a direction perpendicular to the center axis of the rotating cylinder or extending obliquely from the direction.

In the above black roll, thin film forming apparatus, and thin film forming method, preferably, the groove is colored in black.

According to the present invention, the black roll exhibits a function of eliminating almost all reflection of light from the black roll because light made incident on the black roll through the film substrate is trapped in the groove to be decayed and absorbed, thereby making it possible to accurately measure the reflectance of the optical thin film formed on the film substrate in-situ during operation of forming the optical thin film on the film substrate.

DETAILED DESCRIPTION OF THE PREFERRED EMBODIMENT

Hereinafter, a preferred embodiment of the present invention will be described in detail with reference to the accompanying drawings. In the embodiment, the present invention is applicable to measurement of optical characteristics of an optical thin film formed on a film substrate in-situ during operation of forming the optical thin film on the film substrate.

Figure 1A:
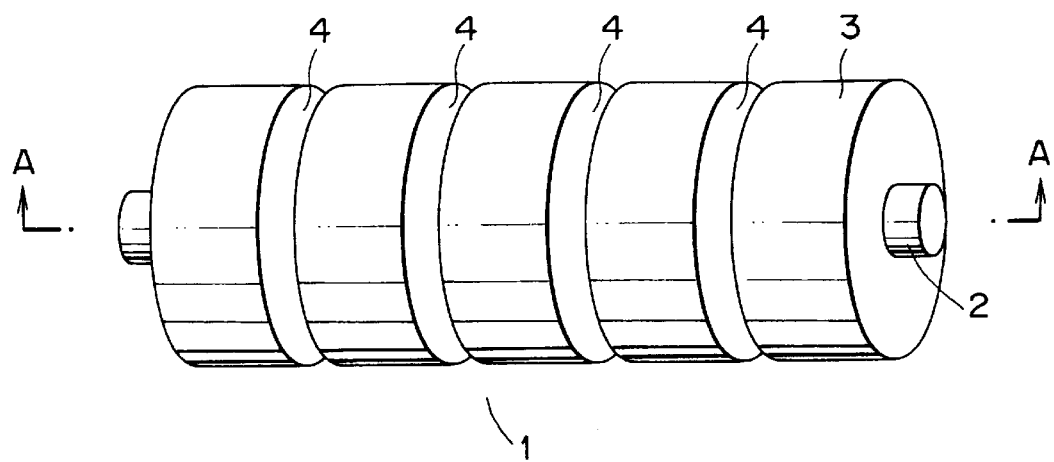
FIG. 1A is a schematic perspective view of a black roll for optical measurement according one embodiment of the present invention.
Figure 1B:
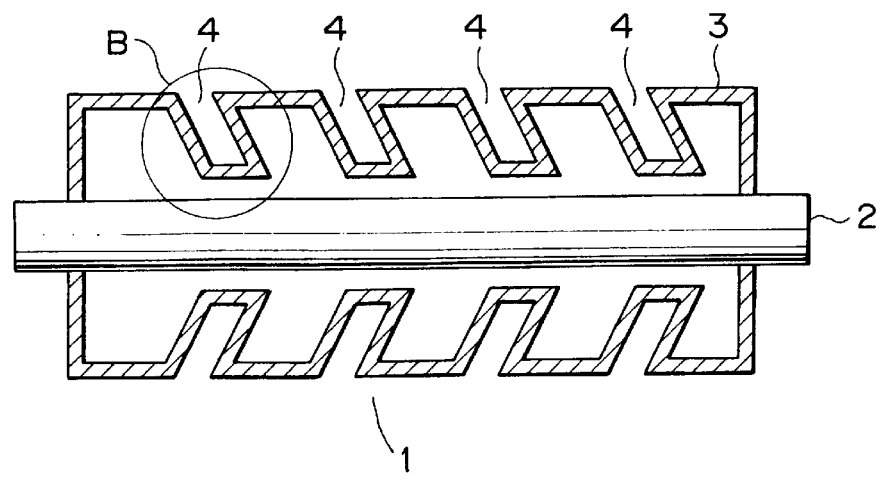
FIG. 1B is a schematic sectional view taken on line A—A of FIG. 1A.
Figure 2:
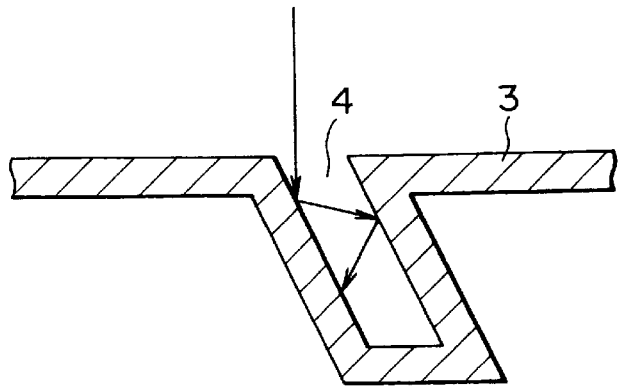
FIG. 2 is a schematic sectional view showing a portion B including a groove formed in the black roll for optical measurement shown in FIG. 1B.
Figure 3A:
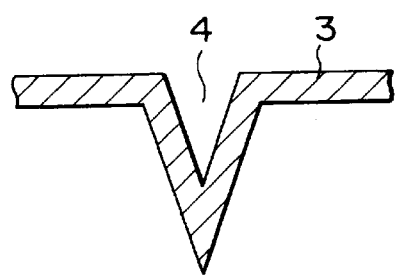
FIGS. 3A to 3C are schematic sectional views each showing a variation of the groove shown in FIG. 2, which is formed in the black roll for optical measurement according to the embodiment of the present invention.
Figure 3B:
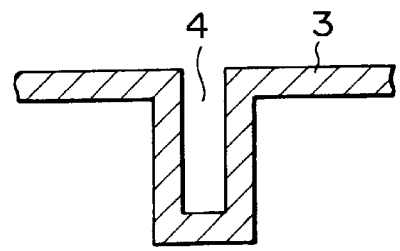
Figure 3C:
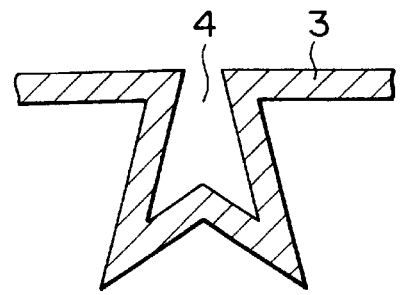
Figure 4:
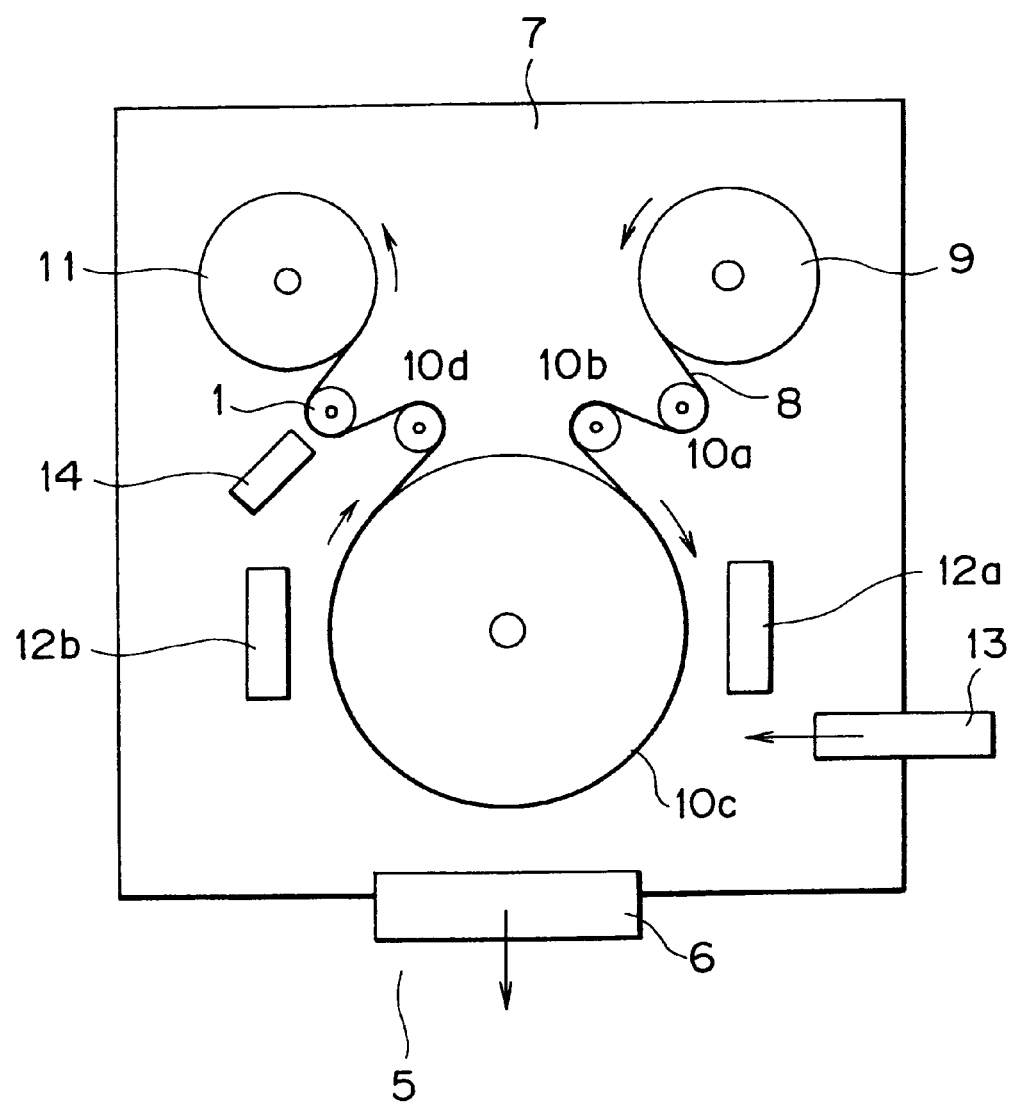
FIG. 4 is a diagram showing one example of an optical thin film forming apparatus including the black roll for optical measurement according to the present invention.

FIG. 1A is a schematic perspective view of a black roll for optical measurement according to one embodiment of the present invention, and FIG. 1B is a schematic sectional view taken on line A—A of FIG. 1A. FIG. 2 is a schematic sectional view of a portion B including a groove shown in FIG. 1B, which is formed in the black roll for optical measurement according to the embodiment of the present invention. FIGS. 3A to 3C are schematic sectional views showing variations of the groove formed in the black roll for optical measurement according to the embodiment of the present invention. FIG. 4 is a schematic diagram showing a thin film forming apparatus including the black roll for optical measurement according to the present invention.

Referring to FIG. 1A, a black roll 1 for optical measurement includes a rotating cylinder 3 having a shaft 2 extending along the center axis of the cylinder 3, and a hard rubber having a smooth surface which is provided on the circumferential surface of the cylinder 3. The surface of the above hard rubber is colored in black for delustering. The rotating cylinder 3 has one or more (four, in this embodiment) grooves 4 formed in the circumferential surface in such a manner as to extend in the circumferential direction. In this embodiment, four optical monitors for measuring optical characteristics such as a reflectance of an optical thin film are arranged in the width direction of a film substrate on which the optical thin film has been formed. To be more specific, the optical monitors (not shown) are disposed in proximity to the four grooves 4 in such a manner as to allow light emitted from the optical monitors to enter in the grooves 4 substantially in the vertical direction with respect to the center axis of the black roll 1. FIG. 1B shows the cross-section of the black roll 1 for optical measurement, taken on a plane containing the center axis of the black roll 1. Referring to FIG. 1B, the cross-section of the groove 4 has a shape formed extending obliquely from the direction perpendicular to the center axis of the rotating cylinder 3.

FIG. 2 is an enlarged view of a portion B including the groove 4 shown in FIG. 1B. Since the cross-section of the groove 4 has the shape extending obliquely from the direction perpendicular to the center axis of the rotating cylinder 3, measuring light which has been emitted from the optical monitor and has entered in the groove 4 through the surface of the rotating cylinder 3 substantially in the vertical direction, is trapped in the groove 4, repeatedly reflected from the inner wall of the groove 4, and finally decayed and absorbed to be thus extinguished.

Variations of the groove 4 will be described with reference to FIGS. 3A to 3C.

FIGS. 3A to 3C are each an enlarged view of the portion B including the groove 4 shown in FIG. 1B. The groove 4 may be configured as a V-shaped groove shown in FIG. 3A, a U-shaped groove shown in FIG. 3B, or an inverse M-shaped groove shown in FIG. 3C. The V-shaped groove can collect light reflected from the black roll into a V-shaped valley. The U-shaped groove is easily formed by machining, but cannot trap 100% of incident light. The inverse M-shaped groove, which is a modification of the V-shaped groove, is not easily formed by machining but can trap a large amount of incident light.

While the structure of the groove 4 formed in the surface of the black roll 1 for optical measurement is described in this embodiment, the present invention is not limited thereto. That is to say, the groove 4 having any structure other than those shown in this embodiment may be formed in the surface of the black roll 1 for optical measurement insofar as the groove 4 thus formed exhibits the same function as that described in this embodiment.

One example of a thin film forming apparatus including the above black roll for optical measurement will be described with reference to FIG. 4. The thin film forming apparatus is used for forming an optical thin film on a film substrate and measuring the reflectance of the optical thin film in-situ.

Referring to FIG. 4, an optical thin film forming apparatus 5 includes a running apparatus disposed in a vacuum chamber 7, the interior of which is evacuated by a vacuum evacuation apparatus 6. The running apparatus is adapted to move, at a constant speed, a film substrate 8 made from a high polymer such as polyethylene terephthalate to a winding roll 11 by way of a feed roll 9, guide rolls 10a, 10b, 10c and 10d, and a black roll 1 for optical measurement. A sputtering system, a vapor-deposition system, or a CVD (Chemical Vapor Deposition) system is used as an evaporation means. An evaporation source 12a of, for example, Si and an evaporation source 12b of, for example, Nb, ITO and Ti, which are materials for forming an optical thin film, are arranged in such a manner as to face to the guide roll 10c. A gas inlet valve 13 is mounted to the vacuum chamber 7 for adjusting the flow rates of reaction gases, such as argon (Ar) gas and oxygen gas, to be supplied in the vacuum chamber 7. While not shown, the guide roll 10c is cooled for preventing temperature rise of the film substrate 8 upon formation of the optical thin film thereon. Here, the black roll 1 for optical measurement includes the above-described rotating cylinder in the surface of which one or more grooves are formed. An optical monitor 14 for measuring optical characteristics is mounted in proximity to a surface portion, with which the film substrate 8 is in close-contact, of the black roll 1 for optical measurement. Specifically, to measure the reflectance of the optical thin film formed on the film substrate 8, the optical monitor 14 is arranged in the proximity to the surface of the black roll 1 for optical measurement in such a manner as to allow measuring light emitted from the optical monitor 14 to enter in the groove formed in the circumferential surface of the black roll 1 for optical measurement substantially in the vertical direction with respect to the center axis of the black roll 1.

One example of a method of forming an optical thin film used as a filter or the like by using the optical thin film forming apparatus 5 will be described below with reference to FIG. 4. First, the film substrate 8 made from a high polymer such as polyethylene terephthalate is set to the feed roll 9, and is wound around the winding roll 11 by way of the guide rolls 10a, 10b, 10c and 10d, and the black roll 1 for optical measurement.

Then, a plurality of layers of $SiO_2$, $Nb_2O_5$, ITO, TiO and TiN are alternately formed by alternately evaporating the evaporation source 12a of Si and the evaporation source 12b of Nb while adjusting the flow rates of the Ar gas and oxygen gas and simultaneously adjusting the film thickness to satisfy a specific reflectance by the optical monitor 14 while adjusting the flow rates of the Ar gas and oxygen gas, to thus form an optical thin film having a previously designed film configuration on the film substrate 8.

By using the black roll 1 for optical measurement in which one or more grooves are formed, it is possible to eliminate all reflection of measuring light from the black roll 1, and hence to accurately measure the reflectance of the optical thin film formed on the film substrate 8 in-situ.

In this embodiment, the optical thin film is formed by alternately forming a plurality of layers of $SiO_2$, $Nb_2O_5$, ITO, TiO and TiN; however, the present invention can be applied to an optical thin film having another function such as a reflection preventive thin film, a wavelength filter, a mirror, or the like.

What is claimed is:

1. A black roll for optical measurement, which is used for a process of moving a film substrate around said black roll, and measuring optical characteristics of a thin film formed on said film substrate by using an optical monitor disposed in proximity to said film substrate, said black roll comprising:

a rotating cylinder colored in black, with the circumferential surface of which said film substrate is in close-contact;

wherein said rotating cylinder has at least one groove formed in said circumferential surface of said rotating cylinder in such a manner as to extend in the circumferential direction, said groove being adapted to absorb light which is emitted from said optical monitor, passing through said film substrate, and is made incident on said black roll.

2. A black roll for optical measurement according to claim 1, wherein the cross-section of said groove, taken along a plane including the center axis of said rotating cylinder, has a shape extending in a direction perpendicular to the center axis of said rotating cylinder or extending obliquely from said direction.

3. A black roll for optical measurement according to claim 1, wherein said groove is colored in black.

4. A thin film forming apparatus including a black roll for optical measurement, which is used for a process of moving a film substrate around said black roll, and measuring optical characteristics of a thin film formed on said film substrate by using an optical monitor disposed in proximity to said film substrate, said black roll comprising:

a rotating cylinder colored in black, with the circumferential surface of which said film substrate is in close-contact;

wherein said rotating cylinder has at least one groove formed in said circumferential surface of said rotating cylinder in such a manner as to extend in the circumferential direction, said groove being adapted to absorb light which is emitted from said optical monitor, passing through said film substrate, and is made incident on said black roll.

5. A thin film forming apparatus according to claim 4, wherein the cross-section of said groove, taken along a plane including the center axis of said rotating cylinder, has a shape extending in a direction perpendicular to the center axis of said rotating cylinder or extending obliquely from said direction.

6. A thin film forming apparatus according to claim 4, wherein said groove is colored in black.

7. A thin film forming method using a black roll for optical measurement, comprising the steps of:

moving a film substrate around said black roll; and measuring optical characteristics of a thin film formed on said film substrate by using an optical monitor disposed in proximity to said film substrate;

wherein said black roll includes a rotating cylinder colored in black, with the circumferential surface of which said film substrate is in close-contact; and said rotating cylinder has at least one groove formed in said circumferential surface of said rotating cylinder in such a manner as to extend in the circumferential direction, said groove being adapted to absorb light which is emitted from said optical monitor, passing through said film substrate, and is made incident on said black roll.

8. A thin film forming method according to claim 7, wherein the cross-section of said groove, taken along a plane including the center axis of said rotating cylinder, has a shape extending in a direction perpendicular to the center axis of said rotating cylinder or extending obliquely from said direction.

9. A thin film forming method according to claim 7, wherein said groove is colored in black.

* * * * *